(12) United States Patent
Yuge et al.

(10) Patent No.: US 12,097,031 B2
(45) Date of Patent: Sep. 24, 2024

(54) EMOTION ESTIMATION APPARATUS AND EMOTION ESTIMATION METHOD

(71) Applicant: Mitsubishi Electric Corporation, Tokyo (JP)

(72) Inventors: Seiro Yuge, Tokyo (JP); Kota Kurihara, Tokyo (JP); Koji Ota, Tokyo (JP); Noriko Nagata, Sanda (JP); Masashi Sugimoto, Sanda (JP); Fan Zhang, Sanda (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 18/278,003

(22) PCT Filed: Mar. 15, 2021

(86) PCT No.: PCT/JP2021/010340
§ 371 (c)(1),
(2) Date: Aug. 21, 2023

(87) PCT Pub. No.: WO2022/195661
PCT Pub. Date: Sep. 22, 2022

(65) Prior Publication Data
US 2024/0032835 A1 Feb. 1, 2024

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0075* (2013.01); *A61B 5/01* (2013.01); *A61B 5/0533* (2013.01);
(Continued)

(58) Field of Classification Search
None
See application file for complete search history.

(56) References Cited

U.S. PATENT DOCUMENTS 10,803,303 B2 10/2020 Komatsuzaki
2012/0308971 A1* 12/2012 Shin ...................... G08B 31/00
434/236
(Continued)

FOREIGN PATENT DOCUMENTS

CN 109643160 A 4/2019
JP 2017-074214 A 4/2017
(Continued)

OTHER PUBLICATIONS

Obata et al., "Construction of customers' emotion model in the bespoke tailoring using evaluation grid method," 2020 IEEE International Conference on Consumer Electronics (ICCE), Las Vegas, NV, USA, 2020, pp. 1-4. (Year: 2020).*
(Continued)

*Primary Examiner* — Yi-Shan Yang
(74) *Attorney, Agent, or Firm* — XSENSUS LLP

(57) ABSTRACT

An emotion estimation apparatus includes preparation biological information acquisition circuitry acquires, separately from subjects who are in a preparation space, first biological information indicating a physical state of each subject and analyzes the first biological information, preparation emotion information acquisition circuitry acquires emotion information indicating an emotion of each of the subjects, association construction circuitry constructs association information in which the first biological information and the emotion information corresponding to the first biological information are associated with each other, estimation biological information acquisition circuitry acquires second biological information indicating a physical state of any one subject of the subjects who is present in an estimation space,
(Continued)

estimation circuitry extracts the emotion information associated in the association information with the first biological information that is equal to the second biological information, and estimate an emotion of the one subject according to the emotion information thus extracted.

20 Claims, 4 Drawing Sheets

(51) Int. Cl.
    *A61B 5/01*         (2006.01)
    *A61B 5/0533*     (2021.01)
    *A61B 5/332*      (2021.01)
    *A61B 5/346*      (2021.01)

(52) U.S. Cl.
    CPC .............. *A61B 5/332* (2021.01); *A61B 5/346* (2021.01); *A61B 5/7278* (2013.01)

(56) References Cited

U.S. PATENT DOCUMENTS

| | | |
|---|---|---|
| 2018/0289266 A1 | 10/2018 | Arai et al. |
| 2019/0187823 A1* | 6/2019 | Kake ................... G06V 40/37 |
| 2019/0236339 A1* | 8/2019 | Komatsuzaki ....... G06V 40/171 |
| 2022/0113816 A1 | 4/2022 | Kake et al. |
| 2024/0008783 A1* | 1/2024 | Palanisamy .......... A61B 5/4803 |

FOREIGN PATENT DOCUMENTS

| | | |
|---|---|---|
| JP | 2018-187044 A | 11/2018 |
| JP | 2019-126657 A | 8/2019 |
| WO | 2018/043061 A1 | 3/2018 |

OTHER PUBLICATIONS

International Search Report and Written Opinion mailed on Jun. 1, 2021, received for PCT Application PCT/JP2021/010340, filed on Mar. 15, 2021, 9 pages including English Translation.

Decision to Grant mailed on Oct. 12, 2021, received for JP Application 2021-550162, filed on Mar. 15, 2021, 5 pages including English Translation.

Office Action issued Apr. 26, 2024 in Chinese Patent Application No. 202180095436.1, 23 pages.

* cited by examiner

EMOTION ESTIMATION APPARATUS AND EMOTION ESTIMATION METHOD

CROSS-REFERENCE TO RELATED APPLICATION

The present application is based on PCT filing PCT/JP2021/010340, filed Mar. 15, 2021, the entire contents of which are incorporated herein by reference.

TECHNICAL FIELD

The present disclosure relates to an emotion estimation apparatus and an emotion estimation method for estimating a human comfortable feeling.

BACKGROUND ART

There have been known apparatuses for estimating human emotions. For example, Patent Literature 1 describes an emotion determination apparatus configured to acquire facial skin temperature data or facial blood circulation data, estimate a subject's brain activity on the basis of the facial skin temperature data or the facial blood circulation data, and determine the subject's emotion on the basis of the brain activity thus estimated.

Specifically, the emotion determination apparatus includes emotion storage circuitry in which results of estimation of brain activity and emotion data representing human emotions are stored in association with each other. The emotion determination apparatus determines the subject's emotion by extracting, from the emotion storage circuitry, emotion data associated with the brain activity estimated on the basis of the facial skin temperature data or the facial blood circulation data. It should be noted that the association between the results of estimation of brain activity and the emotion data stored in the emotion storage circuitry is based, for example, on data on amounts of brain activity gathered by putting persons in any of the states "gladness, anger, sadness, and happiness" and giving them brain function activating assignments for a certain period of time.

CITATION LIST

Patent Literature

Patent Literature 1: Japanese Unexamined Patent Application Publication No. 2017-74214

SUMMARY OF INVENTION

Technical Problem

Note here that the emotion determination apparatus puts the persons in any of the states "gladness, anger, sadness, and happiness" in any way, gathers the data on the amounts of brain activity, and makes an association between the emotion data and the results of estimation of brain activity. That is, the emotion determination apparatus evokes emotional changes in the persons through any external stimuli and constructs a database of association between emotion information indicating emotions thus changed and biological information such as results of estimation of brain activity after the changes in emotion. However, in a case in which the database that is used for estimation of emotion is obtained through experiments in which particular stimuli are applied to the persons, experiments in which particular environmental factors are varied, or other experiments, accurate estimation of emotion may be impossible because of differences between experiment environments and everyday environments, differences among individuals, or other influences.

The present disclosure has been made to solve the aforementioned problem, and has an object to provide an emotion estimation apparatus and an emotion estimation method that may bring about improvement in estimation accuracy with which a subject's emotion is estimated.

Solution to Problem

An emotion estimation apparatus according to an embodiment of the present disclosure is an emotion estimation apparatus configured to estimate emotions of a plurality of subjects who are present in an estimation space, the emotion estimation apparatus including preparation biological information acquisition circuitry configured to acquire and analyze first biological information indicating a physical state of each of the plurality of subjects who are present in a preparation space, preparation emotion information acquisition circuitry configured to acquire emotion information indicating an emotion of each of the plurality of subjects who are present in the preparation space, association construction circuitry configured to construct association information in which the first biological information and the emotion information corresponding to the first biological information are associated with each other, estimation biological information acquisition circuitry configured to acquire and analyze second biological information indicating a physical state of any one subject of the plurality of subjects who is present in the estimation space, and estimation circuitry configured to extract the emotion information associated in the association information with the first biological information that is equal to the second biological information and estimate, according to the emotion information thus extracted, an emotion of the one subject who is in the estimation space.

An emotion estimation method according to an embodiment of the present disclosure is an emotion estimation method that is executed by an emotion estimation apparatus configured to estimate emotions of a plurality of subjects who are present in an estimation space, the emotion estimation method including a preparation biological information acquisition step for acquiring and analyzing first biological information indicating a physical state of each of the plurality of subjects who are present in a preparation space, a preparation emotion information acquisition step for acquiring emotion information indicating an emotion of each of the plurality of subjects who are present in the preparation space, an association construction step for constructing association information in which the first biological information and the emotion information corresponding to the first biological information are associated with each other, an estimation biological information acquisition step for acquiring and analyzing second biological information indicating a physical state of any one subject of the plurality of subjects who is present in the estimation space, and an estimation step for extracting the emotion information associated in the association information with the first biological information that is equal to the second biological information and estimating, according to the emotion information thus extracted, an emotion of the one subject who is in the estimation space.

Advantageous Effects of Invention

An embodiment of the present disclosure makes it possible to provide an emotion estimation apparatus and an emotion estimation method that may bring about improvement in estimation accuracy with which a subject's emotion is estimated.

DESCRIPTION OF EMBODIMENTS

In the following description, an emotion estimation apparatus and an emotion estimation method according to embodiments are described in detail with reference to the drawings.

Embodiment 1

Figure 1:
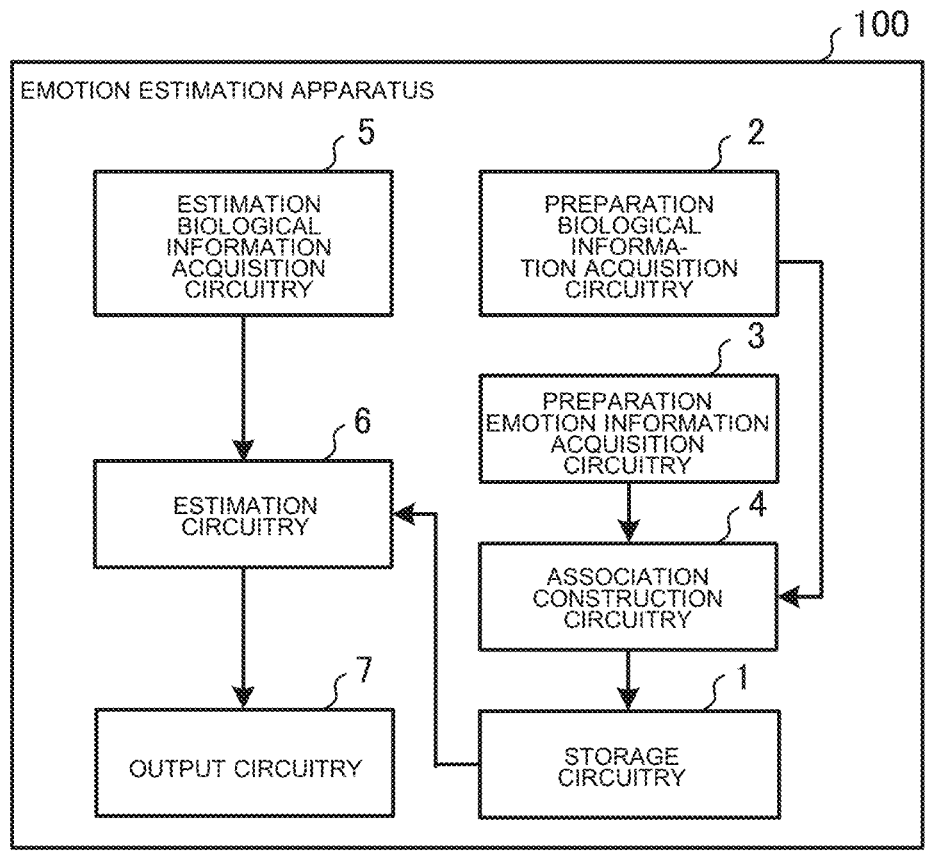
FIG. 1 is a diagram illustrating functional blocks of an emotion estimation apparatus according to Embodiment 1.

An emotion estimation apparatus 100 according to Embodiment 1 is an apparatus by which an emotion of a subject who in a space such as the inside of a particular room such as one room of an office building or a space such as the inside of a house is estimated on the basis of the aftermentioned biological information of the subject. The inside of a particular room or the space such as the inside of a house is hereinafter sometimes referred to as "estimation space". FIG. 1 is a diagram illustrating functional blocks of the emotion estimation apparatus according to Embodiment 1. The emotion estimation apparatus 100 includes storage circuitry 1, preparation biological information acquisition circuitry 2, preparation emotion information acquisition circuitry 3, association construction circuitry 4, estimation biological information acquisition circuitry 5, estimation circuitry 6, and output circuitry 7.

The storage circuitry 1 stores association information with reference to which the emotion estimation apparatus 100 estimates a subject's emotion. The emotion estimation apparatus 100 refers to the association information in estimating a subject's emotion.

The preparation biological information acquisition circuitry 2 includes one or more sensors. The sensors are hereinafter sometimes referred to as "preparation sensors". The preparation biological information acquisition circuitry 2 acquires first biological information as samples through the one or more preparation sensors separately from a plurality of subjects who are present in a preparation space. The preparation space is a space, such as a testing room, in which to acquire the first biological information from the plurality of subjects. The preparation space may be a space that is identical to the aforementioned estimation space, a space in which one stays for the same purpose as the one does in the estimation space, or a space that is similar to the estimation space. The space that is similar to the estimation space may be a space that is different in temperature from the estimation space by a predetermined or lower temperature difference threshold, or may be a space that is different in humidity from the estimation space by a predetermined or lower humidity difference threshold. Alternatively, the similar space may be a space that is different in illuminance from the estimation space by a predetermined or lower illuminance difference threshold, or may be a space that is different in area from the estimation space by a predetermined or lower area difference threshold. The aforementioned similar space is just one example, and the space that is similar to the estimation space is not limited to the aforementioned one. Further, the aforementioned preparation space is just one example, and the preparation space is not limited to the aforementioned one. In a case in which the preparation space is a space that is identical to the aforementioned estimation space, a space in which one stays for the same purpose as the one does in the estimation space, or a space that is similar to the estimation space, the emotion estimation apparatus 100 can acquire the first biological information without placing special burdens on the plurality of subjects. On the other hand, in a case in which the preparation space is not a space that is identical to the aforementioned estimation space, a space in which one stays for the same purpose as the one does in the estimation space, or a space that is similar to the estimation space, it may become easy for the emotion estimation apparatus 100 to acquire the first biological information. The first biological information is information that serves as an index of state of the human body. The first biological information is represented by a numerical value, and changes to various values according to the state of the human body. The first biological information is information that indicates at least one of, for example, body surface temperature, heartbeat, pulse wave, galvanic skin response, an amount of temporal change in body surface temperature, a difference in surface temperature between one of a plurality of regions of the body and another, an index value that is obtained through a frequency analysis of heartbeat, and other parameters. In Embodiment 1, the preparation biological information acquisition circuitry 2 acquires, through the one or more preparation sensors, first biological information indicating at least one of, for example, body surface temperature, heartbeat, pulse wave, galvanic skin response, and other parameters.

The preparation biological information acquisition circuitry 2 may acquire the first biological information through any one type of sensing methods from one portion of the human body. Alternatively, the preparation biological information acquisition circuitry 2 may acquire one type of first biological information or two or more types of first biological information through any two or more types of sensing methods from one portion of the human body. Alternatively, the preparation biological information acquisition circuitry 2 may acquire one type of first biological information or two or more types of first biological information through any two or more types of sensing methods from a plurality of portions of the human body.

In Embodiment 1, the preparation biological information acquisition circuitry 2 analyzes the first biological information acquired through the one or more preparation sensors. Specifically, the preparation biological information acquisition circuitry 2 generates, with use of the first biological information acquired through the one or more preparation sensors, first biological information indicating at least one of an amount of temporal change in body surface temperature, a difference in surface temperature between one of a plurality of regions of the body and another, an index value that is obtained through a frequency analysis of heartbeat, and other parameters. For example, in a case in which the first biological information acquired through the one or more preparation sensors is body surface temperature, the preparation biological information acquisition circuitry 2 may calculate a difference in surface temperature between one of a plurality of regions of the body and another. Alternatively, in a case in which the first biological information acquired through the one or more preparation sensors is data regarding heartbeat, such as electrocardiographic data, the preparation biological information acquisition circuitry 2 may conduct a frequency analysis and acquire an index value indicating a state of heartbeat.

The preparation emotion information acquisition circuitry 3 acquires, from each of the plurality of subjects who are present in the preparation space, emotion information indicating an emotion of each of the plurality of subjects. Note here that the emotion information is information that indicates an emotion such as a degree of comfort, a degree of exaltation, and a degree of sedation and is represented by a numerical value. The preparation emotion information acquisition circuitry 3 includes an input device, such as a keyboard, a touch panel, a button, and a mouse, through which for each of the plurality of subjects to input the emotion information to the emotion estimation apparatus 100.

In Embodiment 1, the preparation emotion information acquisition circuitry 3 acquires the emotion information on the basis of an empirical sampling method from each of the plurality of subjects who are present in the preparation space. That is, the preparation emotion information acquisition circuitry 3 acquires, separately at a plurality of points of time within a predetermined period of time from each of the plurality of subjects who are present in the preparation space, emotion information indicating an emotion of each of the plurality of subjects at each of the plurality of points of time.

The preparation emotion information acquisition circuitry 3 acquires the emotion information on the basis of the empirical sampling method at each of the plurality of points of time in the period of, for example, two or more days. The preparation emotion information acquisition circuitry 3 acquires the emotion information at one or more predetermined times or random times in each day within the period. It is desirable that the preparation emotion information acquisition circuitry 3 acquire the emotion information over a period of five or more days. This is intended for the preparation emotion information acquisition circuitry 3 to evenly acquire emotion information indicating physical and mental states that are brought about by different events that tend to occur every weekday or every day of the week.

The emotion information acquired at each of the plurality of points of time through the empirical sampling method has a reduction in recall bias of each subject. That is, the emotion information acquired at each point of time accurately indicates an emotion of each subject under the influence of an event having occurred at the point of time. Further, a group of pieces of emotion information acquired separately at each of the plurality of points of time is not information that indicates only a particular emotion aroused, for example, by a particular event in everyday life but information that indicates a wide variety of emotions of each subject aroused by a wide variety of events.

The association construction circuitry 4 constructs association information in which first biological information subjected to an analysis by the preparation biological information acquisition circuitry 2 and emotion information corresponding to the first biological information are associated with each other. The "emotion information corresponding to the first biological information" here is information that indicates an emotion, such as the degree of comfort, the degree of exaltation, and the degree of sedation, obtained using emotion information acquired from each subject by the preparation emotion information acquisition circuitry 3 at the same point of time as a point of time at which the preparation biological information acquisition circuitry 2 acquired the first biological information from the subject through the one or more preparation sensors. It should be noted that the "same point of time as a particular point of time" refers to a point of time falling within a predetermined time frame preceding and following the particular point of time. The "predetermined time frame" refers to a time frame, obtained in advance by experiments or other processes, during which there is no change in emotional or physical state of a person.

The emotion information corresponding to the first biological information may be emotion information acquired at the same point of time as a point of time at which the first biological information is acquired, may be obtained through a regression analysis, or may be obtained by averaging values of emotion information for each piece of first biological information. The following gives a description by taking as an example a case in which the first biological information is an amount of temporal change in body surface temperature. For example, in a case in which first biological information indicating 0.5 [degrees C.], i.e., 0.5 degrees Celsius, is acquired from a plurality of subjects, values of emotion information acquired from the plurality of subjects at the same point of time as the 0.5 [degrees C.] is acquired or an average of the values of emotion information is an example of "emotion information corresponding to the first biological information indicating the 0.5 [degrees C.]". Further, in a case in which a relationship between a value of first biological information and a value of emotion information is turned into a mathematical expression through a regression analysis involving the use of values of first biological information and emotion information obtained from a plurality of subjects, a value of emotion information obtained by substituting the 0.5 [degrees C.] into the mathematical expression is an example of "emotion information corresponding to the first biological information indicating the 0.5 [degrees C.]".

The emotion information corresponding to the first biological information is information obtained by generalizing, compared with first biological information indicating physical states of a plurality of subjects, emotions of the plurality of subjects at the same point of time as a point of time at which the first biological information is acquired. For example, in a case in which emotion information that represents a numerical value indicating a high degree of comfort is obtained from a plurality of subjects at all points of time at which the first biological information indicating 0.5 [degrees C.] is acquired from the plurality of subjects, the "emotion information corresponding to the first biological information indicating the 0.5 [degrees C.]" represents a numerical value indicating a high degree of comfort. The high degree of comfort is considered as generally indicating emotions of the plurality of subjects at the points of time at which the first biological information indicating the 0.5 [degrees C.] is acquired.

The association information may for example be a mathematical expression based on the regression analysis that associates the first biological information with the emotion information corresponding to the first biological information. Alternatively, the association information may be information that takes the form of, for example, a table indicating a value of the first biological information and a value of the emotion information corresponding to the first biological information. It should be noted that the association information is not limited to the aforementioned, provided it is information that associates the first biological information with the emotion information corresponding to the first biological information.

The estimation biological information acquisition circuitry 5 includes one or more sensors. The sensors are hereinafter sometimes referred to as "estimation sensors". The one or more estimation sensors may be the same as the aforementioned one or more preparation sensors. The estimation biological information acquisition circuitry 5 acquires second biological information through the one or more estimation sensors from any of the aforementioned plurality of subjects who is present in the estimation space. As mentioned above, the "estimation space" refers to a space in which for the emotion estimation apparatus 100 to estimate an emotion of each of the plurality of subjects. The estimation space may be the same space as or a different space from the preparation space. The second biological information is information that serves as an index of state of the human body. The second biological information is represented by a numerical value, and changes to various values according to the state of the human body. The second biological information is information that indicates at least one of, for example, body surface temperature, heartbeat, pulse wave, galvanic skin response, an amount of temporal change in body surface temperature, a difference in surface temperature between one of a plurality of regions of the body and another, an index value that is obtained through a frequency analysis of heartbeat, and other parameters. In Embodiment 1, the estimation biological information acquisition circuitry 5 acquires, through the one or more estimation sensors, second biological information indicating at least one of, for example, body surface temperature, heartbeat, pulse wave, galvanic skin response, and other parameters.

The estimation biological information acquisition circuitry 5 may acquire the biological information through any one type of sensing methods from one portion of the human body. Alternatively, the estimation biological information acquisition circuitry 5 may acquire one type of biological information or two or more types of biological information through any two or more types of sensing methods from one portion of the human body. Alternatively, the estimation biological information acquisition circuitry 5 may acquire one type of biological information or two or more types of biological information through any two or more types of sensing methods from a plurality of portions of the human body.

In Embodiment 1, the estimation biological information acquisition circuitry 5 analyzes the second biological information acquired through the one or more estimation sensors. Specifically, the estimation biological information acquisition circuitry 5 generates, with use of the second biological information acquired through the one or more estimation sensors, second biological information indicating at least one of an amount of temporal change in body surface temperature, a difference in surface temperature between one of a plurality of regions of the body and another, an index value that is obtained through a frequency analysis of heartbeat, and other parameters. It should be noted that the second biological information that the estimation biological information acquisition circuitry 5 generates is the same type of information as the first biological information that the association information includes. In a case in which the first biological information that the association information includes is an amount of temporal change in body surface temperature, the second biological information that the estimation biological information acquisition circuitry 5 generates is an amount of temporal change in body surface temperature.

The estimation circuitry 6 extracts, with use of the association information, emotion information associated with first biological information that is equal to the second biological information analyzed by the estimation biological information acquisition circuitry 5. In a case in which the association information is information that takes the form of, for example, a table indicating a value of first biological information and a value of emotion information corresponding to the first biological information, the "first biological information that is equal to second biological information" refers to the first biological information that is least different from the second biological information. The estimation circuitry 6 estimates that an emotion indicated by the emotion information thus extracted is an emotion of the subject from whom the second biological information is acquired.

The output circuitry 7 communicates with an external device. An example of the external device is a terminal such as a personal computer, a workstation, a tablet terminal, and a smartphone. Another example of the external device is a display device such as a liquid crystal display, a cathode-ray tube (CRT), and an electroluminescence (organic EL) display. Still another example of the external device is an environmental coordination device, such as an air conditioner and an air purifier, that adjusts an environment of the estimation space. Still another example of the external device is an audio output device including a speaker or other device.

In a case in which the external device is a terminal, the estimation circuitry 6 controls the output circuitry 7 such that the output circuitry 7 sends the emotion information thus extracted to the terminal. In a case in which the external device is a display device, the estimation circuitry 6 controls the output circuitry 7 such that the output circuitry 7 sends, to the display device, the emotion information and display instruction information that instructs the display device to display the emotion information. In a case in which the external device is an environment coordination device, the estimation circuitry 6 controls the output circuitry 7 such that the output circuitry 7 sends, to the environment coordination device, an instruction that causes the environment coordination device to execute an action corresponding to the emotion information and the emotion information. It should be noted that the "action of the environment coordination device corresponding to the emotion information" refers to an action that improves an emotion of a subject in the estimation space. In a case in which the external device is an audio output device, the estimation circuitry 6 controls the output circuitry 7 such that the output circuitry 7 sends, to the audio output device, the emotion information and an instruction to produce audio output of the emotion information.

Figure 2:
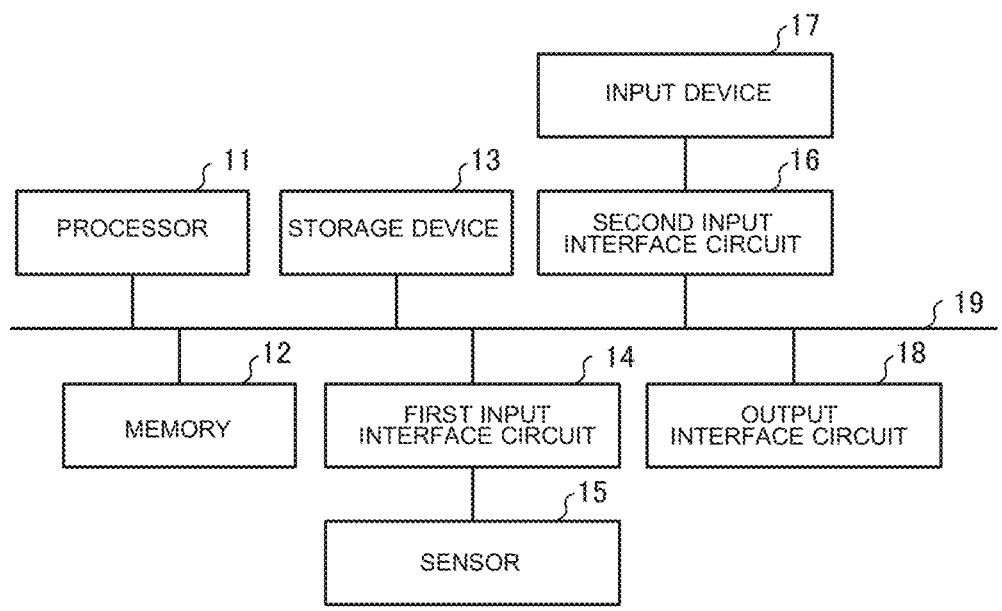
FIG. 2 is a schematic view illustrating a hardware configuration of the emotion estimation apparatus according to Embodiment 1.

The following describes a hardware configuration of the emotion estimation apparatus 100 according to Embodiment 1. FIG. 2 is a schematic view illustrating a hardware configuration of the emotion estimation apparatus according to Embodiment 1. The emotion estimation apparatus 100 may be formed, for example, by a processor 11, a memory 12, a storage device 13, a first input interface circuit 14, a sensor 15, a second input interface circuit 16, an input device 17, an output interface circuit 18, and other device. It should be noted that the processor 11, the memory 12, the storage device 13, the first input interface circuit 14, the second input interface circuit 16, and the output interface circuit 18 are connected by a bus 19.

Examples of the processor 11 include devices such as a central processing unit (CPU) and a micro processing unit (MPU). Examples of the memory 12 include devices such as a read-only memory (ROM) and a random-access memory (RAM). Examples of the storage device 13 include devices such as a hard disk drive (HDD) and a solid state drive (SSD). Examples of the sensor 15 include devices such as an infrared sensor and a wearable sensor. Examples of the input device 17 include devices such as a keyboard and a touch panel. The first input interface circuit 14 is an input interface circuit that mediates between the processor 11 and the sensor 15. The second input interface circuit 16 is an input interface circuit that mediates between the processor 11 and the input device 17.

A function of the storage circuitry 1 can be implemented by the storage device 13. Functions of the association construction circuitry 4 and the estimation circuitry 6 can be implemented by the processor 11 reading out and executing a variety of programs, such as an emotion estimation program for estimating an emotion, stored in the memory 12 or the storage device 13. The function of the preparation biological information acquisition circuitry 2 to acquire first biological information and the function of the estimation biological information acquisition circuitry 5 to acquire second biological information can be implemented by the first input interface circuit 14 and the sensor 15. The function of the preparation biological information acquisition circuitry 2 to analyze first biological information and the function of the estimation biological information acquisition circuitry 5 to analyze second biological information can be implemented by the processor 11 reading out and executing a variety of programs, such as the emotion estimation program, stored in the memory 12 or the storage device 13. The function of the preparation emotion information acquisition circuitry 3 to acquire emotion information at each of the plurality of points of time can be implemented by the processor 11, the second input interface circuit 16, and the input device 17. It should be noted that the function of the association construction circuitry 4 or the preparation emotion information acquisition circuitry 3 to, until the association construction circuitry 4 generates association information, retain emotion information acquired by the preparation emotion information acquisition circuitry 3 from each of the plurality of subjects at each of the plurality of points of time can be implemented by the memory 12 or the storage device 13. The function of the association construction circuitry 4 or the preparation biological information acquisition circuitry 2 to, until the association construction circuitry 4 generates association information, retain first biological information acquired by the preparation biological information acquisition circuitry 2 from each of the plurality of subjects at each of the plurality of points of time and analyzed by the preparation biological information acquisition circuitry 2 can be implemented by the memory 12 or the storage device 13.

A function of the output circuitry 7 can be implemented by the output interface circuit 18. It should be noted that in a case in which the external device is a terminal, the output interface circuit 18 is a communication interface circuit. Meanwhile, in a case in which the external device is any one device of a display device, an audio output device, and an environment coordination device, the output interface circuit 18 is an output interface circuit that mediates between the one device and the processor 11.

The emotion estimation apparatus 100 may include a plurality of the first input interface circuits 14 and a plurality of the sensors 15. This allows the emotion estimation apparatus 100 to, in a case in which a plurality of subjects are in separate places in the preparation space and the estimation space, acquire first biological information and second biological information simultaneously from each of the plurality of subjects. The emotion estimation apparatus 100 may include a plurality of the second input interface circuits 16 and a plurality of the input devices 17. This allows the emotion estimation apparatus 100 to, in a case in which a plurality of subjects are in separate places in the preparation space, acquire emotion information simultaneously from each of the plurality of subjects. All or some functions of the emotion estimation apparatus 100 may be implemented by dedicated hardware.

Figure 3:
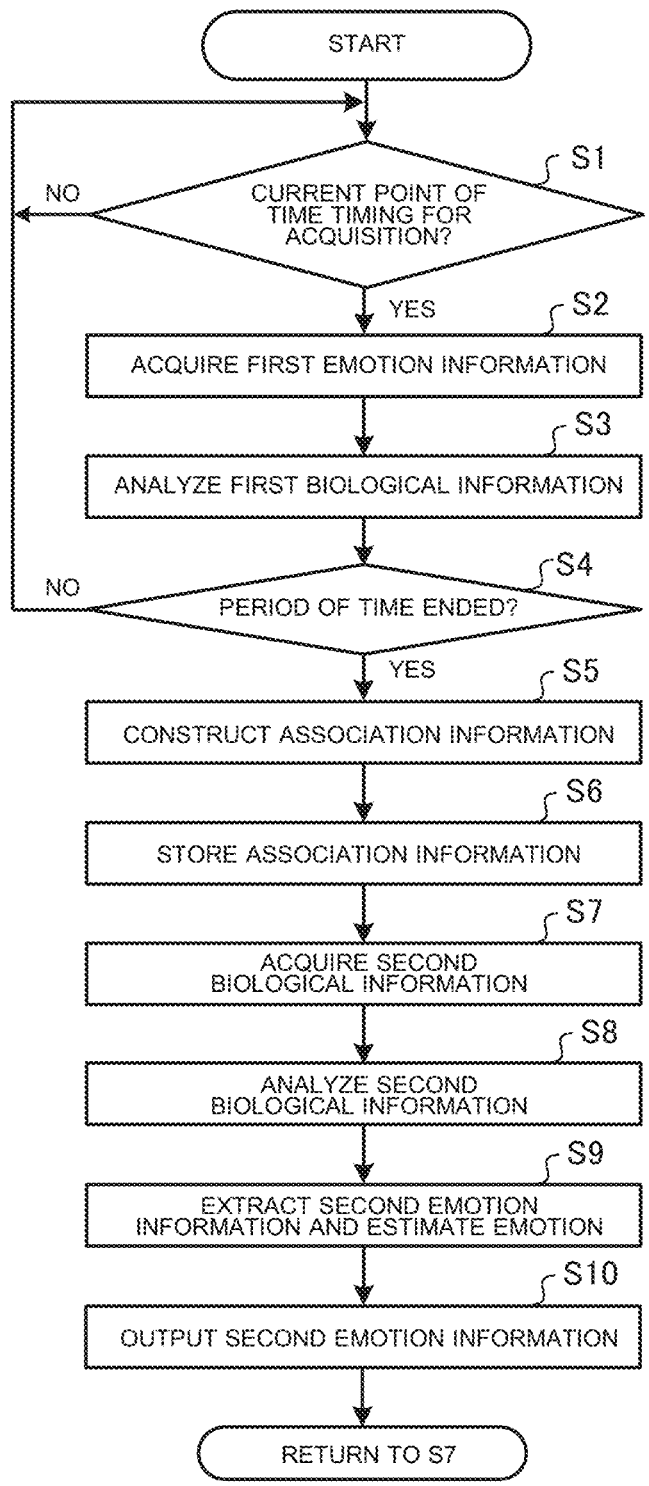
FIG. 3 is a flow chart illustrating an emotion estimation process that is executed by the emotion estimation apparatus according to Embodiment 1.

Next, an emotion estimation process that is executed by the emotion estimation apparatus 100 according to Embodiment 1 is described with reference to FIG. 3. FIG. 3 is a flow chart illustrating an emotion estimation process that is executed by the emotion estimation apparatus according to Embodiment 1. In step S1, the preparation emotion information acquisition circuitry 3 determines whether a current point of time is a timing of acquisition of emotion information. The timing is hereinafter referred to as "timing for acquisition". In a case in which the current point of time is not a timing for acquisition (NO in step S1), the preparation emotion information acquisition circuitry 3 returns the emotion estimation process to step S1.

In a case in which the current point of time is a timing for acquisition (YES in step S1), the preparation emotion information acquisition circuitry 3 proceeds to step S2, in which the preparation emotion information acquisition circuitry 3 acquires emotion information from each of the plurality of subjects. In step S3, the preparation biological information acquisition circuitry 2 analyzes first biological information acquired from each subject at the same point of time as a point of time of acquisition of the emotion information. It should be noted that the preparation biological information acquisition circuitry 2 may be configured to acquire first biological information from each subject at the same point of time as a point of time of acquisition of emotion information, or may be configured to continuously acquire first biological information from each subject. In a case in which the preparation biological information acquisition circuitry 2 is configured to continuously acquire first biological information from each subject, the preparation biological information acquisition circuitry 2 may be configured to analyze the first biological information continuously acquired.

In step S4, the preparation emotion information acquisition circuitry 3 determines whether the period of time has ended. In a case in which the period of time has not ended (NO in step S4), the preparation emotion information acquisition circuitry 3 returns the emotion estimation process to step S1. In a case in which the period of time has ended (YES in step S4), the association construction circuitry 4 proceeds to step S5, in which the association construction circuitry 4 constructs, with use of emotion information and first biological information acquired over the period of time, association information in which first biological information and emotion information corresponding to the first biological information are associated with each other. In step S6, the association construction circuitry 4 stores the association information thus constructed in the storage circuitry 1.

In step S7, the estimation biological information acquisition circuitry 5 acquires second biological information from any of the plurality of subjects. In step S8, the estimation biological information acquisition circuitry 5 analyzes the second biological information thus acquired. In step S9, the estimation circuitry 6 extracts, with reference to the association information, emotion information associated with first biological information that is equal to the second biological information thus analyzed. The estimation circuitry 6 estimates that an emotion indicated by the emotion information thus extracted is the subject's emotion. In step S10, the estimation circuitry 6 instructs the output circuitry 7 to output the emotion information thus extracted to the external device. The output circuitry 7 outputs the emotion information to the external device in accordance with the instruction from the estimation circuitry 6. After processing in step S10, the emotion estimation process ends. In a case in which the emotion estimation process is executed again, the emotion estimation apparatus 100 starts from processing in step S7.

The following describes effects that are brought about by the emotion estimation apparatus 100 according to Embodiment 1. The emotion estimation apparatus 100 according to Embodiment 1 includes the preparation biological information acquisition circuitry 2, the preparation emotion information acquisition circuitry 3, the association construction circuitry 4, the estimation biological information acquisition circuitry 5, and the estimation circuitry 6. The preparation biological information acquisition circuitry 2 acquires and analyzes first biological information indicating physical states of a plurality of subjects who are present in a preparation space. The preparation emotion information acquisition circuitry 3 acquires emotion information indicating an emotion of each of the plurality of subjects who are present in the preparation space. The association construction circuitry 4 constructs association information in which the first biological information and the emotion information corresponding to the first biological information are associated with each other. The estimation biological information acquisition circuitry 5 acquires and analyzes second biological information indicating a physical state of any of the plurality of subjects who is in an estimation space. The estimation circuitry 6 extracts the emotion information associated in the association information constructed by the association construction circuitry 4 with the first biological information that is equal to the second biological information. Then, the estimation circuitry 6 estimates, according to the estimation information thus extracted, an emotion of the subject who is in the estimation space. This brings about improvement in accuracy of emotion estimation.

In Embodiment 1, the association construction circuitry 4 constructs the association information with use of the emotion information acquired from each of the plurality of subjects by the preparation emotion information acquisition circuitry 3 and the first biological information acquired from each of the plurality of subjects by the preparation biological information acquisition circuitry 2 at the same point of time as a point of time at which the emotion information is acquired. It should be noted that the "same point of time as a point of time at which the emotion information is acquired" refers to a point of time falling within a predetermined time frame preceding and following a point of time at which the preparation emotion information acquisition circuitry 3 acquires the emotion information from each of the plurality of subjects. This causes association information to be renewed by emotion information and first biological information acquired immediately before or after a point of time of acquisition of the emotion information, bringing about improvement in accuracy of the association information. This brings about improvement in accuracy of emotion estimation with use of the association information by the emotion estimation apparatus 100.

In Embodiment 1, the preparation emotion information acquisition circuitry 3 acquires, separately at a plurality of points of time within a predetermined period of time from each of the plurality of subjects who are present in the preparation space, the emotion information indicating an emotion of each of the plurality of subjects at each of the plurality of points of time. The association construction circuitry 4 constructs the association information with use of the first biological information acquired from each of the plurality of subjects by the preparation biological information acquisition circuitry 2 at each of the plurality of points of time and the emotion information acquired from each of the plurality of subjects by the preparation emotion information acquisition circuitry 3 at each of the plurality of points of time. This brings about a reduction in recall bias of emotion information that the preparation emotion information acquisition circuitry 3 acquires. Further, a correlation in association information between first biological information and emotion information corresponding to the first biological information is independent from a particular event such as a climate change, a change in physical condition, and a change in sentiment. This reduces the influence of the event on association information, bringing about improvement in accuracy. This brings about improvement in accuracy of emotion estimation by the estimation circuitry 6.

In Embodiment 1, the period of time is a period of five or more days. The preparation emotion information acquisition circuitry 3 acquires the emotion information from each of the plurality of subjects at one or more predetermined times or one or more random times in each day. This makes association information independent from a weather, a physical condition, a sentiment, and other factors in each of the five weekdays, each day of the week, each season, and other periods of time. This reduces the influence of a variety of events on association information, bringing about improvement in accuracy. This brings about improvement in accuracy of emotion estimation by the estimation circuitry 6.

The emotion estimation apparatus 100 according to Embodiment 1 further includes the output circuitry 7 configured to communicate with an external device. The estimation circuitry 6 controls the output circuitry 7 such that the output circuitry 7 sends the emotion information thus extracted to the external device. Thus, in a case in which the external device is a terminal, a display device, or an audio output device, a user of the terminal, the display device, or the audio output device can find out a subject's emotion. Further, in a case in which the external device is the aforementioned environmental coordination device, the environmental coordination device can execute an operation according to the subject's emotion to, for example, improve the degree of comfort of the subject or improve intellectual productivity of the subject, which correlates with the degree of comfort.

Embodiment 2

An emotion estimation apparatus 100 according to Embodiment 2 constructs, for each subject, association information in which first biological information and emotion information corresponding to the first biological information are associated with each other. Moreover, the emotion estimation apparatus 100 estimates each subject's emotion with a higher degree of accuracy with use of the association information. The following describes Embodiment 2. It should be noted that constituent elements of Embodiment 2 that are the same as those of Embodiment 1 are given reference signs that are the same as those of Embodiment 1. Further, contents of Embodiment 2 that are similar to those of Embodiment 1 are not described unless circumstances are exceptional.

Functional blocks included in the emotion estimation apparatus 100 according to Embodiment 2 are similar to the functional blocks, which are illustrated in FIG. 1, in the emotion estimation apparatus 100 according to Embodiment 1.

In Embodiment 2, the preparation biological information acquisition circuitry 2 includes sensors, such as wearable sensors, assigned separately to each of the plurality of subjects. The sensor assigned to each subject is assigned sensor identification information for identifying the sensor. Alternatively, in Embodiment 2, the preparation biological information acquisition circuitry 2 includes a camera and a sensor configured to recognize the face of each of the plurality of subjects. As such, the preparation biological information acquisition circuitry 2 can identify each subject. It should be noted that the preparation biological information acquisition circuitry 2 is not limited to the aforementioned one, provided it can identify each subject.

In Embodiment 2, the preparation emotion information acquisition circuitry 3 includes, for example, terminals assigned separately to each of the plurality of subjects. Each of the terminals is assigned an ID (identifier) for identifying the terminal. Alternatively, in Embodiment 2, the preparation emotion information acquisition circuitry 3 acquires emotion information from each subject and identification information for identifying the subject. The ID of the terminal of each subject, the identification information of the subject, or other identification information and the sensor identification information of the sensor assigned to the subject, data of the face of the subject, or other identification information are associated with each other in the emotion estimation apparatus 100. Pieces of information for identifying each subject such as the ID of the terminal of the subject, the identification information of the subject, the sensor identification information of the sensor assigned to the subject, and the data of the face of the subject are hereinafter collectively referred to as "identification information".

In Embodiment 2, the association construction circuitry 4 generates, for each piece of identification information of a subject, association information in which first biological information indicating a body of the subject and emotion information indicating an emotion of the subject and corresponding to the first biological information are associated with each other. That is, the association construction circuitry 4 generates association information in which identification information of each subject, first biological information indicating a physical state of the subject, and emotion information corresponding to the first biological information indicating the physical state of the subject are associated with one another.

Note here that the emotion information corresponding to the first biological information indicating the physical state of the subject may be emotion information acquired at the same point of time as a point of time at which the first biological information is acquired from the subject. Alternatively, the emotion information corresponding to the first biological information indicating the physical state of the subject may be information obtained through the aforementioned regression analysis or the aforementioned average calculation process with use of emotion information acquired at the same point of time as a point of time at which the first biological information is acquired from the subject. The following gives a description by taking as an example a case in which the first biological information is an amount of temporal change in body surface temperature. In this example, emotion information acquired from a particular subject at the same point of time as a point of time at which first biological information indicating 0.5 [degrees C.] is acquired indicates a high degree of comfort. In this case, a numerical value indicating the high degree of comfort or an average of such numerical values is an example of "emotion information corresponding to an amount of temporal change in body surface temperature, which is 0.5 [degrees C.], of the particular type of subject", that is, "emotion information corresponding to first biological information indicating a physical state of the particular subject". Further, in a case in which a relationship between first biological information and emotion information is turned into a mathematical expression through a regression analysis or other analyses with use of values of first biological information and emotion information obtained from a particular subject, a value of emotion information obtained by substituting the 0.5 [degrees C.] into the mathematical expression is an example of "emotion information corresponding to first biological information indicating a physical state of the particular subject".

The emotion information corresponding to the first biological information indicating the physical state of the subject generally indicates an emotion of the subject. For example, in a case in which emotion information that represents a numerical value indicating a high degree of comfort is obtained from the particular subject at all points of time at which the first biological information indicating 0.5 [degrees C.] is acquired, emotion information corresponding to first biological information indicating a physical state of the particular subject, that is, an amount of temporal change in body surface temperature of 0.5 [degrees C.], indicates a high degree of comfort of the particular subject. The high degree of comfort is considered as generally indicating an emotion of the particular subject at the points of time at which the first biological information indicating the 0.5 [degrees C.] is acquired.

The estimation circuitry 6 extracts emotion information associated in association information with identification information of each subject and first biological information that is equal to second biological information, acquired by the estimation biological information acquisition circuitry 5, that indicates a physical state of the subject. Then, the estimation circuitry 6 estimates that an emotion indicated by the emotion information thus extracted is an emotion of the subject.

Figure 4:
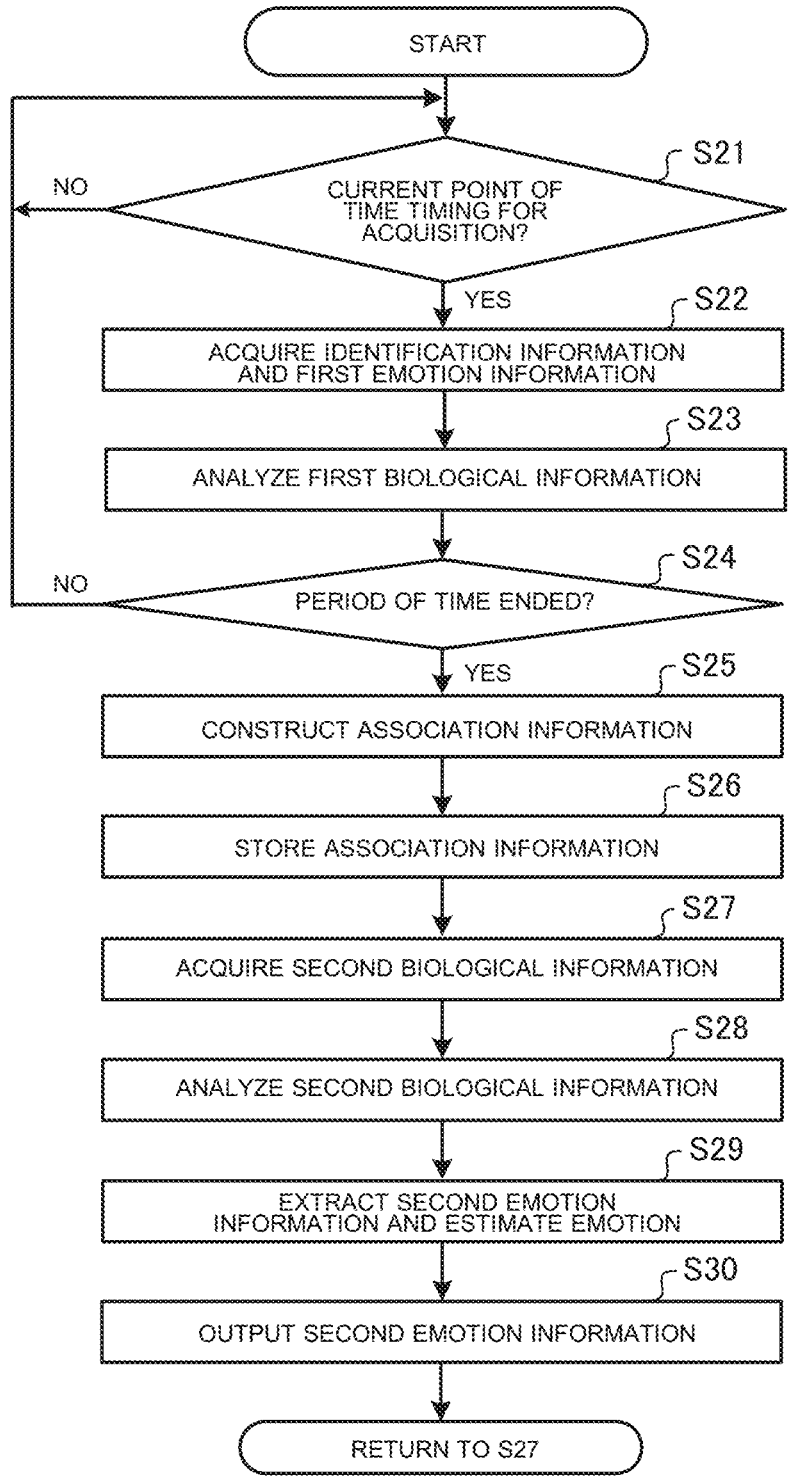
FIG. 4 is a flow chart illustrating an emotion estimation process according to Embodiment 2.

FIG. 4 is a flow chart illustrating an emotion estimation process according to Embodiment 2. Processing in step S21 is not described, as it is the same as the processing in step S1. In a case in which the current point of time is not a timing for acquisition (NO in step S21), the preparation emotion information acquisition circuitry 3 returns the emotion estimation process to step S21. In a case in which, in step S21, the current point of time is a timing for acquisition (YES in step S21), the preparation emotion information acquisition circuitry 3 proceeds to step S22, in which the preparation emotion information acquisition circuitry 3 acquires identification information and emotion information from the plurality of subjects. In step S23, the preparation biological information acquisition circuitry 2 analyzes first biological information acquired from each subject at the same point of time as a point of time at which emotion information is acquired from the subject. It should be noted that the preparation biological information acquisition circuitry 2 acquires, from each subject, first biological information and the identification information such as the sensor identification information for identifying the subject and the face data. The preparation biological information acquisition circuitry 2 may be configured to acquire first biological information from each subject at the same point of time as a point of time of acquisition of emotion information, or may be configured to continuously acquire first biological information from each subject. In a case in which the preparation biological information acquisition circuitry 2 is configured to continuously acquire first biological information from each subject, the preparation biological information acquisition circuitry 2 may be configured to analyze the first biological information continuously acquired.

In step S24, the preparation emotion information acquisition circuitry 3 determines whether the period of time has ended. In a case in which the period of time has not ended (NO in step S24), the preparation emotion information acquisition circuitry 3 returns the emotion estimation process to step S21. In a case in which the period of time has ended (YES in step S24), the association construction circuitry 4 proceeds to step S25, in which the association construction circuitry 4 constructs association information in which identification information of each subject, first biological information indicating a physical state of the subject, and emotion information indicating an emotion of the subject and corresponding to the first biological information are associated with one another. Processing in step S26 is not described, as it is the same as the processing in step S6.

In step S27, the estimation biological information acquisition circuitry 5 acquires second biological information from any of the plurality of subjects. In so doing, the estimation biological information acquisition circuitry 5 acquires the second biological information and the identification information, such as the sensor identification information and the face data, for identifying the subject. Processing in step S28 is not described, as it is the same as the processing in step S8. In step S29, the estimation circuitry 6 extracts, with reference to the association information, emotion information associated with identification information of the subject and first biological information that is equal to the second biological information thus analyzed. The estimation circuitry 6 estimates that an emotion indicated by the emotion information thus extracted is the subject's emotion. Processing in step S30 is not described, as it is the same as the processing in step S10. After processing in step S30, the emotion estimation process ends. In a case in which the emotion estimation process is executed again, the emotion estimation apparatus 100 starts from processing in step S27.

The following describes effects that are brought about by the emotion estimation apparatus 100 according to Embodiment 2. In Embodiment 2, the preparation biological information acquisition circuitry 2 and the preparation emotion information acquisition circuitry 3 acquire identification information for identifying each of the plurality of subjects. The association construction circuitry 4 constructs the association information in which the identification information of each subject, the first biological information indicating a physical state of each subject, and emotion information indicating an emotion of each subject and corresponding to the first biological information indicating the physical state of each subject are associated with one another. The estimation circuitry 6 extracts the emotion information associated in the association information with the identification information of any the subjects and the first biological information that is equal to the second biological information indicating a physical state of the subject, and estimates an emotion of the subject according to the emotion information thus extracted. As such, the association information indicates a correlation between a physical state and an emotion for each subject. The estimation circuitry 6 thus can estimate an emotion for each subject with use of the association information. Therefore, the emotion estimation apparatus 100 can estimate an emotion with a high degree of accuracy according to each subject in spite of the differences in characteristic among the subjects, for example regardless of whether the subjects are sensitive to heat or sensitive to cold.

Embodiment 3

An emotion estimation apparatus 100 according to Embodiment 3 is configured to acquire emotion information on the basis of an evaluation grid method in the construction of estimating information and conduct a cluster analysis to categorize the subjects. The following describes Embodiment 3. It should be noted that constituent elements of Embodiment 3 that are the same as those of Embodiments 1 and 2 are given reference signs that are the same as those of Embodiments 1 and 2. Further, contents of Embodiment 3 that are similar to those of Embodiments 1 and 2 are not described unless circumstances are exceptional.

Functional blocks included in the emotion estimation apparatus 100 according to Embodiment 3 are similar to the functional blocks, which are illustrated in FIG. 1, in the emotion estimation apparatuses 100 according to Embodiments 1 and 2.

In Embodiment 3, the preparation emotion information acquisition circuitry 3 acquires emotion information from each of the plurality of subjects on the basis of the evaluation grid method. In this case, the preparation emotion information acquisition circuitry 3 acquires, as emotion information on the basis of a grading method, a comfort level that serves as an index for a degree of comfort. Further, in addition to a comfort level, the preparation emotion information acquisition circuitry 3 acquires, on the basis of a free descriptive method, factor information indicating a factor of the comfort level.

The association construction circuitry 4 conducts a cluster analysis with use of a comfort level and factor information acquired by the preparation emotion information acquisition circuitry 3. Specifically, the association construction circuitry 4 categorizes each subject into any of a plurality of types with use of factor information from each subject. For example, the association construction circuitry 4 categorizes, for example as "hyperthermic type", a subject whose comfort level is mainly due to a hyperthermic factor. Further, the association construction circuitry 4 categorizes, for example as "internal type", a subject whose comfort level is mainly due to an internal factor such as physical and mental states. Furthermore, the association construction circuitry 4 categorizes, for example as "balanced type", a subject whose comfort level is affected by various factors. Note here that what factor affects the comfort level of each subject is determined by factor information acquired from the subject. For example, the contents of a predetermined or higher proportion of factor information from a particular subject concern temperature, the association construction circuitry 4 categorizes the particular subject, for example, as the "hyperthermic type". It should be noted that although, in Embodiment 3, the predetermined proportion is 70% or 80%, it may be 50%, 60%, or other proportions. The number of types, the names of types, or other attributes of types are not limited to the aforementioned ones but can be set as appropriate.

The association construction circuitry 4 may categorize each subject into a type as described above according to factor information from each subject and analyze, according to a comfort level from each subject, what and to what extent each subject feels comfortable or uncomfortable. For example, in a case in which factor information from a particular subject indicates coldness and a comfort level acquired together with the factor information from the particular subject is low, the association construction circuitry 4 may analyze the particular subject as "cold-sensitive type". Moreover, the association construction circuitry 4 may conduct more detailed categorization than in a case in which only factor information is used. For example, the association construction circuitry 4 may categorize the particular subject as "hyperthermic type" and "cold-sensitive type". Further, the association construction circuitry 4 may categorize each subject with use of biological information from each subject as well as factor information from each subject. For example, in a case in which biological information from a particular subject indicates low body temperature and factor information acquired at the same point of time as a point of time at which the biological information is acquired from the particular subject indicates "coldness", the association construction circuitry 4 may analyze the particular subject as "cold-natured type".

In Embodiment 3, the association construction circuitry 4 constructs association information in which type information indicating a type, first biological information indicating a physical state of one or more subjects of the type, and emotion information corresponding to the first biological information indicating the physical state of the one or more subjects are associated with one another. It should be noted that the emotion information corresponding to the first biological information indicating the physical state of the one or more subjects of the type may be emotion information acquired at the same time as a point of time at which the first biological information is acquired from the one or more subjects. Alternatively, the emotion information corresponding to the first biological information indicating the physical state of the one or more subjects may be obtained through the aforementioned regression analysis or the aforementioned average calculation process with use of emotion information acquired at the same point of time as a point of time at which the first biological information is acquired from the one or more subjects. The emotion information corresponding to the first biological information indicating the physical state of the one or more subjects of the type generally indicates an emotion of the one or more subjects of the type.

The following gives a description by taking as an example a case in which the first biological information is an amount of temporal change in body surface temperature. In this example, in a case in which there are five subjects categorized into a particular type, emotion information acquired from the five subjects at the same point of time as a point of time at which first biological information indicating 0.5 [degrees C.] is acquired indicates a high degree of comfort. In this case, a numerical value indicating the high degree of comfort or an average of such numerical values is an example of "emotion information corresponding to amounts of temporal change in body surface temperature, which are 0.5 [degrees C.], of the five subjects of the particular type", that is, "emotion information corresponding to biological information indicating physical states of the five subjects of the particular type". Further, in a case in which a relationship between first biological information and emotion information is turned into a mathematical expression through a regression analysis or other analyses with use of values of first biological information and emotion information obtained from the five subjects, a value of emotion information obtained by substituting the 0.5 [degrees C.] into the mathematical expression is an example of "emotion information corresponding to biological information indicating physical states of the five subjects of the particular type". The high degree of comfort is considered as generally indicating emotions of the five subjects of the particular type at the point of time at which the first biological information indicating the 0.5 [degrees C.] is acquired.

In Embodiment 3, the association construction circuitry 4 may construct association information in which identification information of each subject, type information indicating a type of the subject, first biological information indicating a physical state of the subject, and emotion information corresponding to the first biological information indicating the physical state of the subject are associated with one another.

In a case in which type information, first biological information, emotion information corresponding to the first biological information are associated with one another in association information, the estimation circuitry 6 extracts emotion information associated with first biological information that is equal to second biological information acquired by the estimation biological information acquisition circuitry 5. It should be noted that in Embodiment 3, type information is uniquely determined by a value of first biological information. The estimation circuitry 6 may extract type information associated with first biological information that is equal to the second biological information and estimate a type of the subject from whom the second biological information is acquired.

In a case in which identification information, type information, first biological information, emotion information corresponding to the first biological information are associated with one another in association information, the estimation circuitry 6 extracts emotion information associated with identification information acquired by the estimation biological information acquisition circuitry 5 and first biological information that is equal to second biological information acquired by the estimation biological information acquisition circuitry 5. The estimation circuitry 6 may extract type information associated with the identification information and first biological information that is equal to the second biological information and estimate a type of the subject from whom the second biological information is acquired.

In a case in which type information is extracted, the estimation circuitry 6 instructs the output circuitry 7 to output the type information thus extracted to an external device. The output circuitry 7 outputs the type information to the external device. In a case in which the external device is the aforementioned display device, type information acquired from the output circuitry 7 is displayed. In a case in which the external device is the aforementioned audio output device, type information acquired from the output circuitry 7 is output in the form of sound. In a case in which the external device is the aforementioned terminal, type information acquired from the output circuitry 7 is displayed or output in the form of sound. A subject is thus allowed to find out a type of the subject. It should be noted that a subject can also find out a type of the subject with reference to the storage circuitry 1 with use of the terminal connected to the emotion estimation apparatus 100.

In a case in which a subject knows a type of the subject, the subject may input type information indicating the type to an unillustrated input device such as a keyboard and a touch panel in acquiring second biological information. Moreover, the estimation circuitry 6 may extract identification information of the subject and the type information or emotion information associated with the type information and estimate an emotion of the subject.

Figure 5:
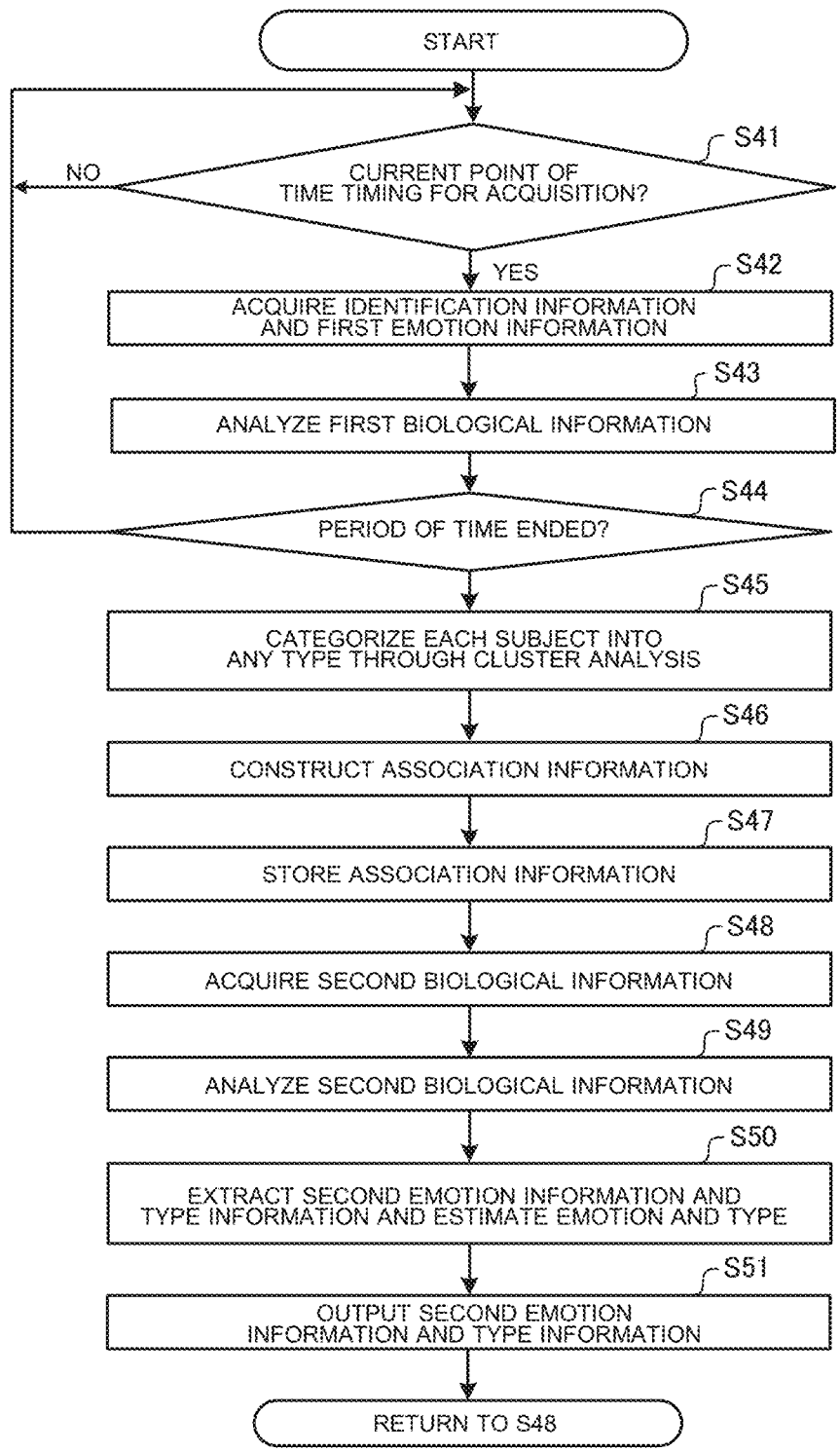
FIG. 5 is a flow chart illustrating an emotion estimation process according to Embodiment 3.

FIG. 5 is a flow chart illustrating an emotion estimation process according to Embodiment 3. A description is given here by taking as an example a case in which the preparation biological information acquisition circuitry 2 and the preparation emotion information acquisition circuitry 3 acquire identification information for identifying each subject. Processing in steps S41 to S44 is not described, as it is the same as the processing in steps S21 to S24.

In a case in which the preparation emotion information acquisition circuitry 3 has determined in step S44 that the period of time has ended (YES in step S44), the association construction circuitry 4 proceeds to step S45, in which the association construction circuitry 4 conducts a cluster analysis and categorizes each subject into any of a plurality of types. In step S46, the association construction circuitry 4 constructs association information in which type information, first biological information indicating a physical state of one or more subjects of a type indicated by the type information, and emotion information indicating an emotion of the one or more subjects and corresponding to the first biological information are associated with one another. Alternatively, in step S46, the association construction circuitry 4 constructs association information in which identification information of each subject, type information indicating a type of the subject, first biological information indicating a physical state of the subject, and emotion information indicating an emotion of the subject and corresponding to the first biological information are associated with one another. Processing in step S47 is not described, as it is the same as the processing in step S6. Processing in step S48 is not described, as it is the same as the processing in step S7 and step S27. Processing in step S49 is not described, as it is the same as the processing in step S8.

In step S50, the estimation circuitry 6 extracts emotion information and type information both associated with first biological information that is equal to second biological information analyzed in step S49. Alternatively, the estimation circuitry 6 extracts emotion information and type information both associated with identification information for identifying any of the subjects from whom the second biological information is acquired and first biological information that is equal to the second biological information. In step S51, the estimation circuitry 6 instructs the output circuitry 7 to output the emotion information thus extracted and the type information thus extracted to an external device. After processing in step S51, the emotion estimation process ends. In a case in which the emotion estimation process is executed again, the emotion estimation apparatus 100 starts from processing in step S48.

The following describes effects that are brought about by an emotion estimation apparatus 200 according to Embodiment 3. In Embodiment 3, the preparation emotion information acquisition circuitry 3 acquires, as the emotion information from each of the plurality of subjects on the basis of an evaluation grid method, a comfort level indicating a degree of comfort of each of the plurality of subjects and acquires factor information indicating a factor of the comfort level of each of the plurality of subjects. The preparation emotion information acquisition circuitry 3 acquires the comfort level on the basis of a grading method and acquires the factor information on the basis of a free descriptive method. The association construction circuitry 4 conducts a cluster analysis with use of the factor information from each of the plurality of subjects and categorizes each of the plurality of subjects into any of a plurality of types. The association construction circuitry 4 constructs the association information in which type information indicating the type, first biological information indicating a physical state of one or more of the plurality of subjects categorized into the type, and emotion information indicating an emotion of the one or more subjects and corresponding to the first biological information indicating the physical state of the one or more subjects are associated with one another. The estimation circuitry 6 extracts the emotion information and the type information both associated in the association information with the first biological information that is equal to the second biological information indicating a physical state of any of the subjects. The estimation circuitry 6 estimates an emotion of the subject according to the emotion information thus extracted and estimates the type of the subject according to the type information thus extracted. As such, the association information indicates a correlation between first biological information and emotion information peculiar to a type such as a "hyperthermic type" and an "internal type". The estimation circuitry 6 thus can estimate an emotion of a subject with a high degree of accuracy with use of second biological information according to a type of the subject.

In Embodiment 3, the preparation emotion information acquisition circuitry 3 acquires, as the emotion information from each of the plurality of subjects on the basis of an evaluation grid method, a comfort level indicating a degree of comfort of each of the plurality of subjects and acquires factor information indicating a factor of the comfort level of each of the plurality of subjects. The preparation emotion information acquisition circuitry 3 acquires the comfort level on the basis of a grading method and acquires the factor information on the basis of a free descriptive method. The preparation biological information acquisition circuitry 2 and the preparation emotion information acquisition circuitry 3 acquire identification information for identifying each of the plurality of subjects. The association construction circuitry 4 conducts a cluster analysis with use of the factor information from each of the plurality of subjects and categorizes each of the plurality of subjects into any of a plurality of types. The association construction circuitry 4 constructs the association information in which the identification information of each of the plurality of subjects, type information indicating the type of each of the plurality of subjects, first biological information indicating a physical state of each of the plurality of subjects, and emotion information indicating an emotion of each of the plurality of subjects and corresponding to the first biological information indicating the physical state of each of the plurality of subjects are associated with one another. The estimation circuitry 6 extracts the emotion information and the type information both associated in the association information with the identification information of any of the subjects and the first biological information that is equal to the second biological information. The estimation circuitry 6 estimates an emotion of the subject according to the emotion information thus extracted and estimates the type of the subject according to the type information thus extracted. As such, the association information indicates a correlation between a physical state and an emotion for each subject. The estimation circuitry 6 thus can estimate an emotion for each subject with use of the association information. Therefore, the emotion estimation apparatus 100 can estimate an emotion with a high degree of accuracy according to a type for each subject.

In Embodiment 3, the association construction circuitry 4 conducts a cluster analysis with use of at least either the first biological information from each subject or the comfort level from each subject as well as the factor information from each subject and categorizes each subject into any of the plurality of types. As such, the association construction circuitry 4 can categorize each subject in detail into a type. This brings about further improvement in accuracy of the association information. This brings about improvement in accuracy of emotion estimation by the emotion estimation apparatus 100.

The emotion estimation apparatus 100 according to Embodiment 3 further includes the output circuitry 7 configured to communicate with an external device. The estimation circuitry 6 controls the output circuitry 7 such that the output circuitry 7 sends the emotion information thus extracted and the type information thus extracted to the external device. Thus, a user of the external device, such as a terminal, a display device, and an audio output device can find out an emotion and a type of any of the subjects. In a case in which the user is the subject, the subject can find out a type of the subject.

Embodiment 4

An emotion estimation apparatus 100 according to Embodiment 4 is configured to estimate a subjects emotion with a higher degree of accuracy. The following describes Embodiment 4, It should be noted that constituent elements of Embodiment 4 that are the same as those of Embodiments 1 to 3 are given reference signs that are the same as those of Embodiments 1 to 3. Further, contents of Embodiment 4 that are similar to those of Embodiments 1 to 3 are not described unless circumstances are exceptional.

Functional blocks included in the emotion estimation apparatus 100 according to Embodiment 4 are similar to the functional blocks, which are illustrated in FIG. 1, in the emotion estimation apparatuses 100 according to Embodiments 1 to 3. It should be noted that in Embodiment 4, the preparation emotion information acquisition circuitry 3 acquires emotion information in the same manner as in Embodiment 1.

Of those pieces of biological information that indicate a physical state of a person, a difference from face temperature at rest, a temperature difference between the cheek and the forehead, a value of an electrocardiographic index, or a value indicating galvanic skin response strongly correlates with the person's emotion. In Embodiment 4, the preparation biological information acquisition circuitry 2 acquires first biological information including at least one of, for example, face temperature, electrocardiographic data, and galvanic skin response data of each of the plurality of subjects. The preparation biological information acquisition circuitry 2 senses the face temperature, for example, through an infrared sensor. Further, the preparation biological information acquisition circuitry 2 acquires the electrocardiographic data or the galvanic skin response data, for example, through a wearable sensor.

The preparation biological information acquisition circuitry 2 calculates, on the basis of the first biological information thus acquired, first biological information including at least one of a difference from face temperature at rest, a temperature difference between the cheek and the forehead, a value of an electrocardiographic index, and a value indicating galvanic skin response of each of the plurality of subjects. It should be noted that in a case in which the preparation biological information acquisition circuitry 2 calculates a difference from face temperature at rest, the preparation biological information acquisition circuitry 2 acquires the face temperature at rest in advance.

The estimation biological information acquisition circuitry 5 acquires second biological information including at least one of, for example, face temperature, electrocardiographic data, and galvanic skin response data of any of the plurality of subjects. The estimation biological information acquisition circuitry 5 senses the face temperature, for example, through an infrared sensor. Further, the estimation biological information acquisition circuitry 5 acquires the electrocardiographic data or the galvanic skin response data, for example, through a wearable sensor.

The estimation biological information acquisition circuitry 5 calculates, on the basis of the second biological information thus acquired, second biological information including at least one of a difference from face temperature at rest, a temperature difference between the cheek and the forehead, a value of an electrocardiographic index, and a value indicating galvanic skin response of the subject.

A preferred example of the electrocardiographic index is a high-frequency band, a low-frequency band, an ultralow-frequency band, or a heartbeat interval standard deviation because such an electrocardiographic index strongly correlates with emotion. Further, a preferred example of the value indicating galvanic skin response is an amount of sweating, response amplitude, appearance frequency, response time, or recovery time because such a value strongly correlates with emotion.

An emotion estimation process that is executed by the emotion estimation apparatus 100 according to Embodiment 4 is the same as the emotion estimation processes according to Embodiments 1 to 3, which have been described with reference to FIGS. 3 to 5, except for the following features.

The following describes effects that are brought about by the emotion estimation apparatus 100 according to Embodiment 4. The preparation biological information acquisition circuitry 2 acquires the first biological information including face temperature of each of the plurality of subjects. The preparation biological information acquisition circuitry 2 calculates, with use of the face temperature of each subject, the first biological information including a difference of the face temperature of the subject from the face temperature of the subject at rest or a temperature difference between the cheek and the forehead of the subject. The association construction circuitry 4 constructs the association information in which the first biological information calculated by the preparation biological information acquisition circuitry 2 and emotion information corresponding to the first biological information are associated with each other. The estimation biological information acquisition circuitry 5 acquires the second biological information including face temperature of any of the plurality of the subjects. The estimation biological information acquisition circuitry 5 calculates, with use of the face temperature of the subject, the second biological information including a difference of the face temperature of the subject from the face temperature of the subject at rest or a temperature difference between the cheek and the forehead of the subject. The estimation circuitry 6 extracts the emotion information associated with the first biological information that is equal to the second biological information calculated by the estimation biological information acquisition circuitry 5 and estimates an emotion of the subject according to the emotion information thus extracted. The difference from face temperature at rest and the temperature difference between the cheek and the forehead strongly correlate with emotion. For this reason, using the difference or the temperature difference as the first biological information and the second biological information brings about improvement in accuracy of emotion estimation by the emotion estimation apparatus 100.

In Embodiment 4, the preparation biological information acquisition circuitry 2 acquires the first biological information including electrocardiographic data of each of the plurality of subjects. The preparation biological information acquisition circuitry 2 calculates, with use of the electrocardiographic data of each subject, the first biological information including a value of an electrocardiographic index of the subject. The association construction circuitry 4 constructs the association information in which the first biological information calculated by the preparation biological information acquisition circuitry 2 and emotion information corresponding to the first biological information are associated with each other. The estimation biological information acquisition circuitry 5 acquires the second biological information including electrocardiographic data of any of the plurality of subjects. The estimation biological information acquisition circuitry 5 calculates, with use of the electrocardiographic data of the subject, the second biological information including a value of an electrocardiographic index of the subject. The estimation circuitry 6 extracts the emotion information associated with the first biological information that is equal to the second biological information calculated by the estimation biological information acquisition circuitry 5 and estimates an emotion of the subject according to the emotion information thus extracted. The electrocardiographic index strongly correlates with emotion. For this reason, using the electrocardiographic index as the first biological information and the second biological information brings about improvement in accuracy of emotion estimation by the emotion estimation apparatus 100.

In Embodiment 4, the preparation biological information acquisition circuitry 2 acquires the first biological information including galvanic skin response data of each of the plurality of subjects. The preparation biological information acquisition circuitry 2 calculates, with use of the galvanic skin response data of each subject, the first biological information including a value indicating galvanic skin response of the subject. The association construction circuitry 4 constructs the association information in which the first biological information calculated by the preparation biological information acquisition circuitry 2 and emotion information corresponding to the first biological information are associated with each other. The estimation biological information acquisition circuitry 5 acquires the second biological information including galvanic skin response data of any of the plurality of subjects. The estimation biological information acquisition circuitry 5 calculates, with use of the galvanic skin response data of the subject, the second biological information including a value indicating galvanic skin response of the subject. The estimation circuitry 6 extracts the emotion information associated with the first biological information that is equal to the second biological information calculated by the estimation biological information acquisition circuitry 5 and estimates an emotion of the subject according to the emotion information thus extracted. The galvanic skin response strongly correlates with emotion. For this reason, using the galvanic skin response as the first biological information and the second biological information brings about improvement in accuracy of emotion estimation by the emotion estimation apparatus 100.

The preparation biological information acquisition circuitry 2 and the estimation biological information acquisition circuitry 5 each include a wearable sensor. As such, the preparation biological information acquisition circuitry 2 can acquire the first biological information on a daily basis from each of the plurality of subjects. The association information thus indicates in detail a correlation between a physical state and emotion of each subject in everyday life. Further, the estimation biological information acquisition circuitry 5 can acquire the second biological information in everyday life of any of the subjects. This allows the emotion estimation apparatus 100 to estimate a subject's emotion in everyday life with a high degree of accuracy.

While the foregoing has described embodiments, the contents of the present disclosure are not limited to these embodiments and encompass an envisioned range of equivalents.

REFERENCE SIGNS LIST

1: storage circuitry, 2: preparation biological information acquisition circuitry, 3: preparation emotion information acquisition circuitry, 4: association construction circuitry, 5: estimation biological information acquisition circuitry, 6: estimation circuitry, 7: output circuitry, 11: processor, 12: memory, 13: storage device, 14: first input interface circuit, 15: sensor, 16: second input interface circuit, 17: input device, 18: output interface circuit, 19: bus, 100: emotion estimation apparatus

The invention claimed is:

1. An emotion estimation apparatus configured to estimate emotions of a plurality of subjects when present in an estimation space, the emotion estimation apparatus comprising:

preparation biological information acquisition circuitry configured to acquire and analyze first biological information indicating physical states of the plurality of subjects when the plurality of subjects are present in a preparation space;

preparation emotion information acquisition circuitry configured to acquire emotion information indicating emotions of the plurality of subjects when the plurality of subjects are present in the preparation space;

association construction circuitry configured to construct association information in which the first biological information and the emotion information are associated with each other;

estimation biological information acquisition circuitry configured to acquire and analyze second biological information indicating a physical state of one subject of the plurality of subjects when the one subject is present in the estimation space;

estimation circuitry configured to use the second biological information to extract the emotion information associated in the association information with the first biological information and estimate, according to the emotion information thus extracted, an emotion of the one subject when the one subject is in the estimation space, wherein the preparation emotion information acquisition circuitry is further configured to acquire, as the emotion information from the plurality of subjects on a basis of an evaluation grid method, a comfort level indicating a degree of comfort of each of the plurality of subjects and factor information indicating a factor of the comfort level of each of the plurality of subjects, and the estimation circuitry is further configured to, based on the emotion of the one subject estimated by the estimation circuitry, control an output circuitry to output an instruction that causes an environmental coordination device to execute an action that improves the emotion of the one subject in the estimation space.

2. The emotion estimation apparatus of claim 1, wherein the association construction circuitry is configured to construct the association information with use of the emotion information acquired from the plurality of subjects by the preparation emotion information acquisition circuitry and the first biological information acquired from the plurality of subjects by the preparation biological information acquisition circuitry within a predetermined time frame preceding and following a point of time at which the preparation emotion information acquisition circuitry acquires the emotion information from the plurality of subjects.

3. The emotion estimation apparatus of claim 1, wherein
the preparation emotion information acquisition circuitry is configured to acquire, separately at a plurality of points of time within a period of time that is predetermined, the plurality of subjects who are present in the preparation space, the emotion information indicating the emotions of the plurality of subjects at each of the plurality of points of time, and
the association construction circuitry is configured to construct the association information with use of the first biological information acquired from the plurality of subjects by the preparation biological information acquisition circuitry at each of the plurality of points of time and the emotion information acquired from the plurality of subjects by the preparation emotion information acquisition circuitry at each of the plurality of points of time.

4. The emotion estimation apparatus of claim 3, wherein the period of time is a period of two or more days, and the preparation emotion information acquisition circuitry is configured to acquire the emotion information from the plurality of subjects at one or more predetermined times or one or more random times in each day.

5. The emotion estimation apparatus of claim 4, wherein the period of time is a period of five or more days.

6. The emotion estimation apparatus of claim 1, wherein the preparation emotion information acquisition circuitry is configured to acquire the comfort level on a basis of the evaluation grid method and acquire the factor information on the basis of a free descriptive method.

7. The emotion estimation apparatus of claim 1, wherein
the association construction circuitry is configured to conduct a cluster analysis with use of the factor information from the plurality of subjects, categorize the plurality of subjects into any one type of a plurality of types, and construct the association information in which type information indicating the one type, the first biological information indicating the physical state of one or more subjects of the plurality of subjects categorized into the one type, and the emotion information indicating the emotion of the one or more subjects and corresponding to the first biological information indicating the physical state of the one or more subjects are associated with one another, and
the estimation circuitry is configured to extract the emotion information and the type information both associated in the association information with the first biological information that is equal to the second biological information indicating a physical state of one subject of the plurality of subjects, estimate the emotion of the one subject according to the emotion information thus extracted, and estimate the one type of the one subject according to the type information thus extracted.

8. The emotion estimation apparatus of claim 7, wherein the association construction circuitry is configured to conduct a cluster analysis with use of at least either the first biological information from the plurality of subjects or the comfort level from the plurality of subjects as well as the factor information from the plurality of subjects and categorize the plurality of subjects into the one type of the plurality of types.

9. The emotion estimation apparatus of claim 7, further comprising output circuitry configured to communicate with an external device, wherein the estimation circuitry is configured to control the output circuitry such that the output circuitry sends the emotion information thus extracted and the type information thus extracted to the external device.

10. The emotion estimation apparatus of claim 1, wherein
the preparation biological information acquisition circuitry and the preparation emotion information acquisition circuitry are configured to acquire identification information for identifying the plurality of subjects,
the association construction circuitry is configured to conduct a cluster analysis with use of the factor information from the plurality of subjects, categorize the plurality of subjects into any one type of a plurality of types, and construct the association information in which the identification information of the plurality of subjects, type information indicating the one type of the plurality of subjects, the first biological information indicating the physical states of the plurality of subjects, and the emotion information indicating the emotions of the plurality of subjects and corresponding to the first biological information indicating the physical states of the plurality of subjects are associated with one another, and
the estimation circuitry is configured to extract the emotion information and the type information both associated in the association information with the identification information of one subject of the plurality of subjects and the first biological information that is equal to the second biological information, estimate the emotion of the one subject according to the emotion information thus extracted, and estimate the one type of the one subject according to the type information thus extracted.

11. The emotion estimation apparatus of claim 1, further comprising output circuitry configured to communicate with an external device, wherein the estimation circuitry is configured to control the output circuitry such that the output circuitry sends the emotion information thus extracted to the external device.

12. The emotion estimation apparatus of claim 1, wherein
the preparation biological information acquisition circuitry and the preparation emotion information acquisition circuitry are configured to acquire identification information for identifying the plurality of subjects, the association construction circuitry is configured to construct the association information in which the identification information of the plurality of subjects, the first biological information indicating the physical states of the plurality of subjects, and emotion information indicating the emotions of the plurality of subjects and corresponding to the first biological information indicating the physical states of the plurality of subjects are associated with one another, and the estimation circuitry is configured to extract the emotion information associated in the association information with the identification information of one subject of the plurality of subjects and the first biological information that is equal to the second biological information, and estimate the emotion of the one subject according to the emotion information thus extracted.

13. The emotion estimation apparatus of claim 1, wherein
the preparation biological information acquisition circuitry is configured to acquire the first biological information including face temperature of the plurality of subjects and calculate, with use of the face temperature of the plurality of subjects, the first biological information including a difference of the face temperature of the plurality of subjects from the face temperature of the plurality of subjects at rest or a temperature difference between a cheek and a forehead of the plurality of subjects, the association construction circuitry is configured to construct the association information in which the first biological information calculated by the preparation biological information acquisition circuitry and the emotion information corresponding to the first biological information calculated by the preparation biological information acquisition circuitry are associated with each other, the estimation biological information acquisition circuitry is configured to acquire the second biological information including face temperature of one subject of the plurality of subjects and calculate, with use of the face temperature of the one subject, the second biological information including a difference of the face temperature of the one subject from the face temperature of the one subject at rest or the temperature difference between the cheek and the forehead of the one subject, and the estimation circuitry is configured to extract the emotion information associated with the first biological information that is equal to the second biological information calculated by the estimation biological information acquisition circuitry and estimate the emotion of the one subject according to the emotion information thus extracted.

14. The emotion estimation apparatus of claim 13, wherein
the preparation biological information acquisition circuitry and the estimation biological information acquisition circuitry each include an infrared sensor, and the infrared sensor is configured to sense the face temperature.

15. The emotion estimation apparatus of claim 1, wherein
the preparation biological information acquisition circuitry is configured to acquire the first biological information including electrocardiographic data of the plurality of subjects and calculate, with use of the electrocardiographic data of the plurality of subjects, the first biological information including a value of an electrocardiographic index of the plurality of subjects, the association construction circuitry is configured to construct the association information in which the first biological information calculated by the preparation biological information acquisition circuitry and the emotion information corresponding to the first biological information calculated by the preparation biological information acquisition circuitry are associated with each other, the estimation biological information acquisition circuitry is configured to acquire the second biological information including electrocardiographic data of one subject of the plurality of subjects and calculate, with use of the electrocardiographic data of the one subject, the second biological information including a value of an electrocardiographic index of the one subject, and the estimation circuitry is configured to extract the emotion information associated with the first biological information that is equal to the second biological information calculated by the estimation biological information acquisition circuitry and estimate the emotion of the one subject according to the emotion information thus extracted.

16. The emotion estimation apparatus of claim 15, wherein the preparation biological information acquisition circuitry and the estimation biological information acquisition circuitry each include a wearable sensor.

17. The emotion estimation apparatus of claim 1, wherein
the preparation biological information acquisition circuitry is configured to acquire the first biological information including galvanic skin response data of the plurality of subjects and calculate, with use of the galvanic skin response data of the plurality of subjects, the first biological information including a value indicating galvanic skin response of the plurality of subjects, the association construction circuitry is configured to construct the association information in which the first biological information calculated by the preparation biological information acquisition circuitry and the emotion information corresponding to the first biological information calculated by the preparation biological information acquisition circuitry are associated with each other, the estimation biological information acquisition circuitry is configured to acquire the second biological information including galvanic skin response data of one subject of the plurality of subjects and calculate, with use of the galvanic skin response data of the one subject, the second biological information including a value indicating galvanic skin response of the one subject, and the estimation circuitry is configured to extract the emotion information associated with the first biological information that is equal to the second biological information calculated by the estimation biological information acquisition circuitry and estimate the emotion of the one subject according to the emotion information thus extracted.

18. The emotion estimation apparatus of claim 1, wherein the estimation space includes an inside of a house, and the preparation space includes a testing room.

19. An emotion estimation method that is executed by an emotion estimation apparatus configured to estimate emotions of a plurality of subjects who are present in an estimation space, the emotion estimation method comprising:
- acquiring and analyzing first biological information indicating physical states of the plurality of subjects when the plurality of subjects are present in a preparation space;
- acquiring emotion information indicating emotions of the plurality of subjects when the plurality of subjects are present in the preparation space;
- constructing association information in which the first biological information and the emotion information corresponding to the first biological information are associated with each other;
- acquiring and analyzing second biological information indicating a physical state of one subject of the plurality of subjects when the one subject is present in the estimation space;
- using the second biological information to extract the emotion information associated in the association information with the first biological information; and
- estimating, according to the emotion information thus extracted, an emotion of the one subject when the one subject is in the estimation space;
- acquiring, as the emotion information from each of the plurality of subjects on a basis of an evaluation grid method, a comfort level indicating a degree of comfort of the plurality of subjects, and factor information indicating a factor of the comfort level of the plurality of subjects,
- outputting an instruction, based on the emotion of the one subject estimated by the estimation circuitry, to cause an action that improves the emotion of the one subject in the estimation space.

20. A non-transitory computer-readable medium encoded with computer-readable instructions that, when executed by a processor an emotion estimation apparatus configured to estimate emotions of a plurality of subjects when present in an estimation space, cause the processor to perform an emotion estimation method, comprising:
- acquiring and analyzing first biological information indicating physical states of the plurality of subjects when the plurality of subjects are present in a preparation space;
- acquiring emotion information indicating emotions of the plurality of subjects when the plurality of subjects are present in the preparation space;
- constructing association information in which the first biological information and the emotion information corresponding to the first biological information are associated with each other;
- acquiring and analyzing second biological information indicating a physical state of one subject of the plurality of subjects when the one subject is present in the estimation space;
- using the second biological information to extract the emotion information associated in the association information with the first biological information; and
- estimating, according to the emotion information thus extracted, an emotion of the one subject when the one subject is in the estimation space,
- acquiring, as the emotion information from each of the plurality of subjects on a basis of an evaluation grid method: a comfort level indicating a degree of comfort of the plurality of subjects, and factor information indicating a factor of the comfort level of the plurality of subjects,
- outputting an instruction, based on the emotion of the one subject estimated by the estimation circuitry, to cause an action that improves the emotion of the one subject in the estimation space.

* * * * *